United States Patent
Drummond et al.

(10) Patent No.: US 9,591,846 B2
(45) Date of Patent: Mar. 14, 2017

(54) APPARATUS AND METHOD FOR SEPARATING AND STORING HUMAN REPRODUCTIVE MATERIAL IN A CRYOTANK

(76) Inventors: Michael Drummond, Malvern, PA (US); Jack A. Walker, Jr., Kennett Square, PA (US); Scott Ferguson, Springfield, PA (US)

( * ) Notice: Subject to any disclaimer, the term of this patent is extended or adjusted under 35 U.S.C. 154(b) by 1260 days.

(21) Appl. No.: 11/833,122

(22) Filed: Aug. 2, 2007

(65) Prior Publication Data
US 2009/0035744 A1    Feb. 5, 2009

(51) Int. Cl.
*A01N 1/02*    (2006.01)
*A61B 17/435*    (2006.01)

(52) U.S. Cl.
CPC .......... *A01N 1/0268* (2013.01); *A61B 17/435* (2013.01)

(58) Field of Classification Search
CPC ....... A61J 7/0053; B01L 3/021–3/0213; B01L 3/022; A61D 19/00–19/04; A61B 17/42–17/48; A61B 2017/4216–2017/447; A61M 5/31531
USPC ...... 422/501–526; 600/33–35; 222/206–215; 73/864.01–864.25; 141/24
See application file for complete search history.

(56) References Cited

U.S. PATENT DOCUMENTS

| | | | |
|---|---|---|---|
| 1,963,886 A * | 6/1934 | Chilson | 141/24 |
| 3,244,173 A * | 4/1966 | Berg | 604/192 |
| 3,748,909 A * | 7/1973 | Kuo | 73/864.11 |
| 4,009,260 A | 2/1977 | Ericsson | |
| 4,310,013 A | 1/1982 | McClaskey | |
| 4,589,421 A * | 5/1986 | Ullman | A61B 5/1411 422/503 |
| 5,073,347 A | 12/1991 | Garren et al. | |
| 2004/0259072 A1* | 12/2004 | Kuwayama et al. | 435/1.3 |

OTHER PUBLICATIONS

International Search Report and Written Opinion of the International Searching Authority dated Oct. 22, 2008 in PCT Appln. No. PCT/US 08/71930.

* cited by examiner

*Primary Examiner* — Catherine B Kuhlman
(74) *Attorney, Agent, or Firm* — Ryder, Lu, Mazzeo & Konieczny LLC; Joseph M. Konieczny Sr.; Gregory J. Gore

(57) ABSTRACT

Apparatus and method for separating individual human reproductive material from a fertilization dish and storing the material in a cryotank for future fertilization and implantation. The apparatus includes an elongate cryostraw having a first open end and second heat-sealable open end, a channel extending between said ends, and an internal, calibrated volume VC. A displacement bulb is connected to the first end of the cryostraw for admitting and emitting the material into said cryostraw. The bulb has a total volume VB1, an internal cavity with a compressible end volume VB2, a first seal with the first end of said cryostraw; and, means for limiting the intake volume displacement produced in said cryostraw to an amount less than VC no matter how far the bulb is squeezed. The bulb produces less than a unit volume of displacement in the cryostraw when the bulb is squeezed and its volume VB1 is reduced by a unit volume.

24 Claims, 12 Drawing Sheets

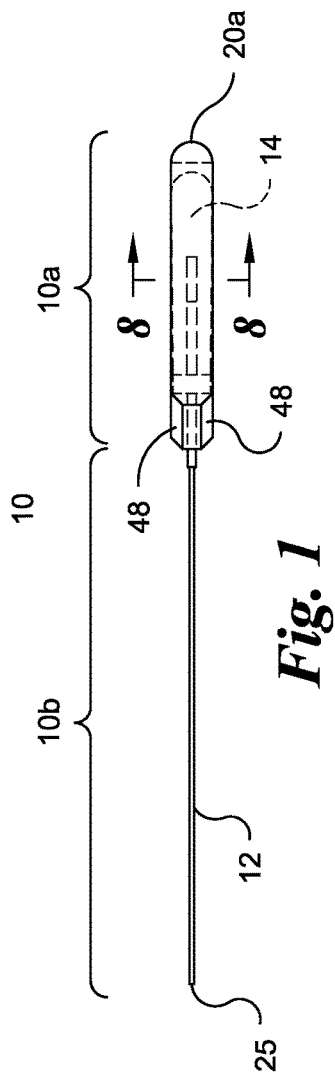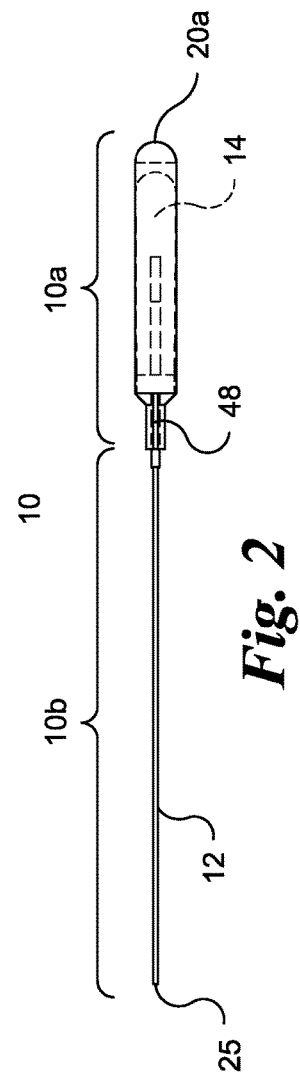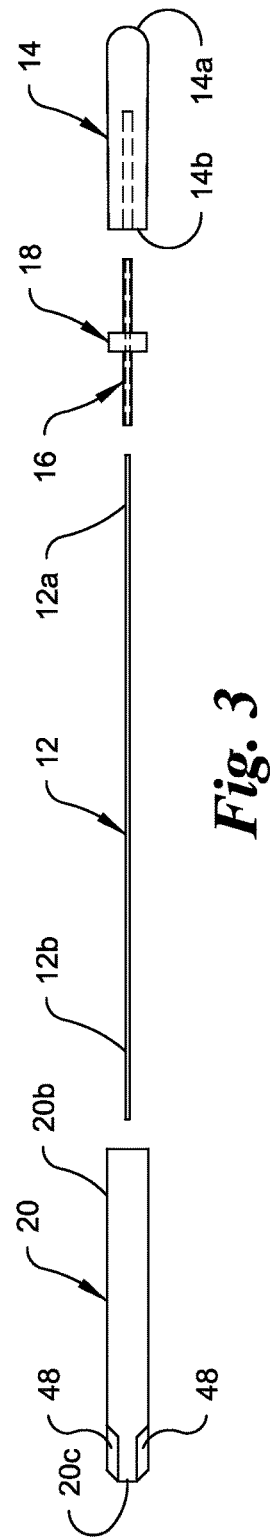

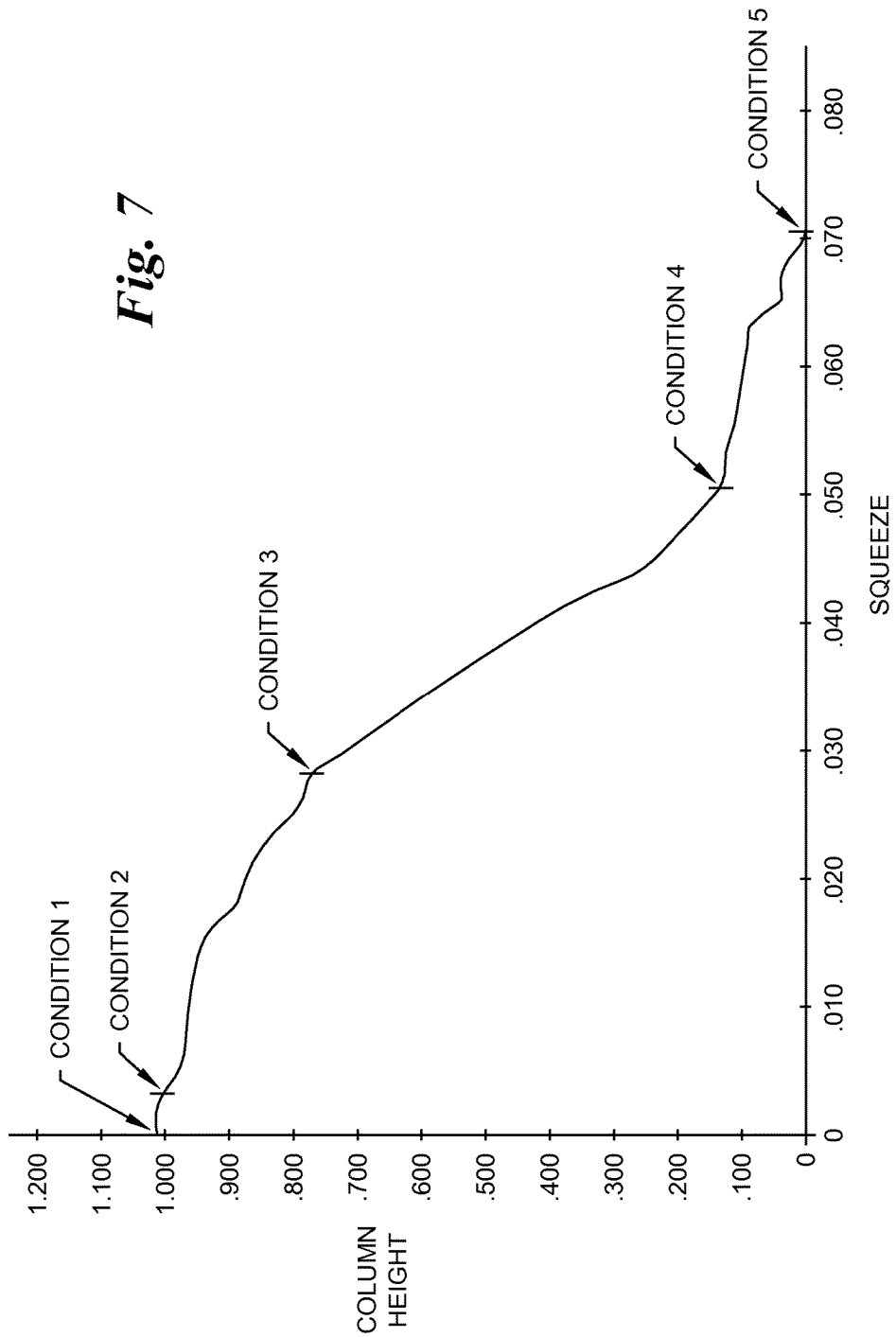

CONDITION 1

CONDITION 2

CONDITION 3

CONDITION 4

CONDITION 5

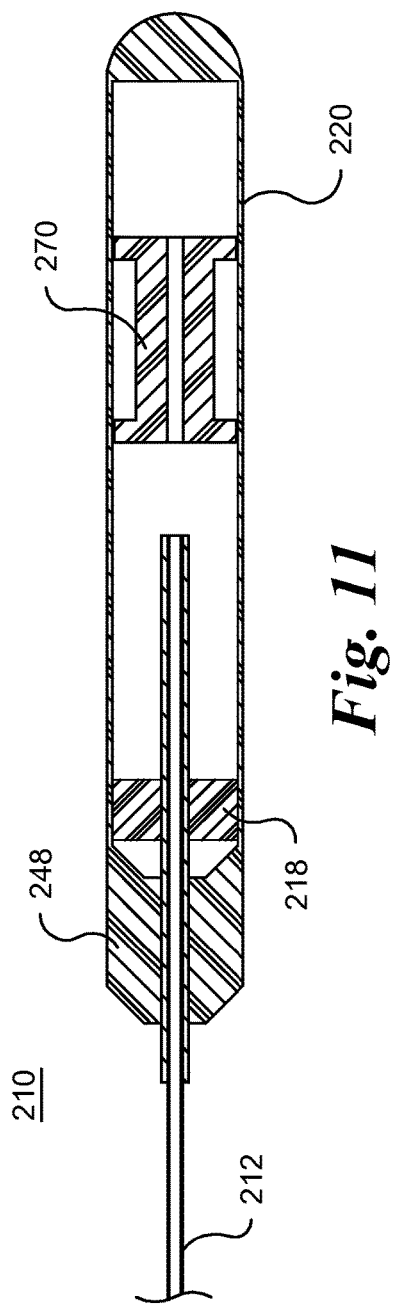
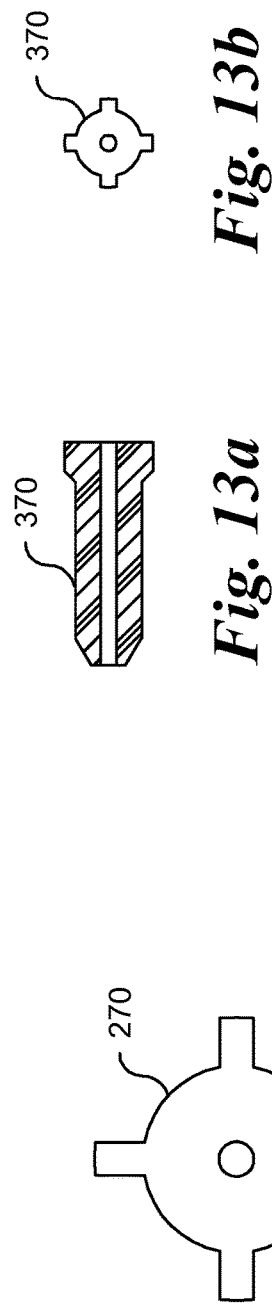
*Fig. 11*
*Fig. 13a*
*Fig. 13b*
*Fig. 14a*
*Fig. 14b*
*Fig. 12*

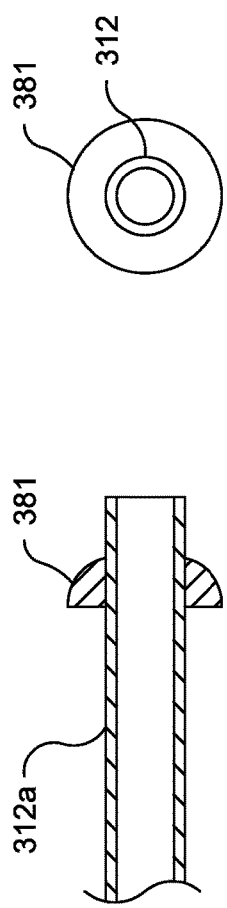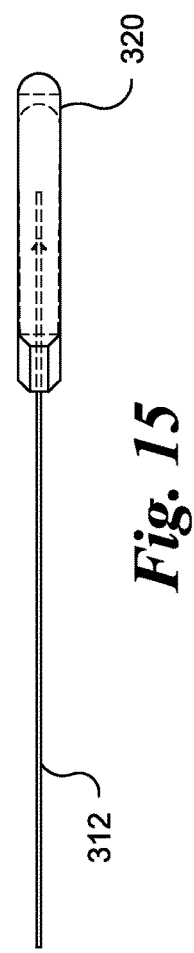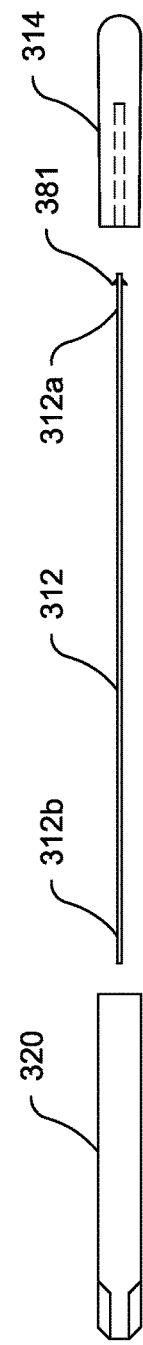

APPARATUS AND METHOD FOR SEPARATING AND STORING HUMAN REPRODUCTIVE MATERIAL IN A CRYOTANK

FIELD OF THE INVENTION

The present invention relates to an apparatus and method for separating individual reproductive material, such as human eggs, blastocysts, and embryos, from a fertilization dish and storing the material in a cryotank for future fertilization and implantation.

BACKGROUND OF THE INVENTION

For a variety of reasons, many people desire to preserve reproductive material for future fertilization and implantation. For example, women cancer patients undergoing chemotherapy or radiation therapy often have a plurality of eggs aspirated from their ovaries and frozen in a cryobank in the event their eggs in ovaria become sterile. There are known, efficient techniques for aspirating eggs from human ovaries and for artificially fertilizing the eggs in a clinic. However, once extracted, known devices and methods for separating the individual eggs, blastocysts or embryos (hereinafter individually and/or collectively referred to as "human reproductive material"or "material") from the fertilization dish and then storing the material are cumbersome and inefficient.

In the prior art, it is known to admit and freeze human reproductive material within open-ended, elongate cryostraws. Often, hundreds of such cryostraws are stored within a single cryotank. This method is potentially hazardous due to the risk of contamination from one egg/embryo to another within the tank. Recently, the FDA has mandated that cryobanks must store each material individually in sealed containers. Therefore, it is desirable to provide an apparatus and method for storing human reproductive material in individually-sealed containers to prevent the risk of contamination in a cryobank.

A known kit for individually separating and storing human reproductive material is sold by Irvine Scientific® under catalog no. 90133DE. The kit includes a cryostraw in which the material is admitted. However, one end of the cryostraw must first be connected to a flexible connection tube, which is provided in the kit. Then, the second end of the connection tube must be connected to a Hamilton syringe, which is not provided in the kit. This assembly is cumbersome to maneuver and requires two hands to assemble and to operate.

Another known kit for embryo cryopreservation is sold by Cryo Bio System ("CBS") under the name CBS High Security Straw System ("HSSS"). This kit also requires assembly of a filing nozzle to the first end of the cryostraw and a connection nozzle to the second end. An aspiration apparatus (not provided) must then be connected to the connection nozzle via a flexible connection tube. This assembly is also cumbersome to maneuver and requires two hands to assemble and to operate. Therefore, it is desirable to provide a separation and storage apparatus that is pre-assembled, fully integrated, and can be operated using a single hand.

It is also very difficult to control displacement in the cryostraw of the above-described devices since the volume of the cryostraw is very small compared to the displacement volume of the Hamilton syringe and/or other aspiration apparatus. Even a small displacement of the aspiration apparatus produces a relatively large volumetric displacement in the cryostraw. Without tedious and careful control of the syringe, it is very easy to over admit the cryostraw. Therefore, it is desirable to provide a separation and storage apparatus that has precise volumetric-displacement control and can not be over admitted.

Once the human reproductive material is admitted to the cryostraw of the Irvine Scientific device or the CBS HSSS device, both ends must be heated sealed by contacting a heated surface. To heat seal the second end, the connection tube must be removed without disturbing or spilling the contents of the cryostraw. This procedure also requires two hands. Further, absent a glaring, visually-discernable defect in one of the seals, there is no practical way to confirm the integrity of each seal on the cryostraw. Therefore, it would be desirable to provide a separation and storage apparatus, which can be easily sealed and tested for seal integrity using a single hand.

Another cryopreservation kit, which is sold by CBS under the name High Security Vitrification Kit ("HSVK"), includes cryostraw, a capillary tube with a pre-formed gutter at one end and a handling rod at the other end, and a plastic insertion and removing device. The HSVK kit requires the technician to initially pick up the material using a micropipette and then to deposit the material onto the gutter of the capillary tube. The HSVK kit also has many of the same deficiencies as the above-described kits.

SUMMARY OF THE INVENTION

The invention provides an apparatus for separating and storing human reproductive material for future fertilization and implantation. The apparatus is fully integrated, can be operated using a single hand, and has precise volumetric-displacement control. The apparatus has means for regulating the amount of displacement produced by the bulb so that the cryostraw can not be over admitted. Once filled with material, the apparatus can be easily sealed. In one embodiment, the apparatus includes integrated means for testing the integrity of the seal using a single hand.

In a preferred embodiment, the apparatus includes an elongate cryostraw having first and second open ends, a constant-diameter channel extending between the ends, and an internal, calibrated volume VC. A displacement bulb is connected to the first end of the cryostraw for admitting and emitting material through the cryostraw.

The bulb preferably comprises a solid mass of compressible material having first and second axial ends, an outer radius R1 and a length L1. A bore extends axially in the first end. The bore has a length L2 that is less than L1 and a radius R2 that is less than R1. The cryostraw has a base portion that is inserted a predetermined distance L3 into the bore so that the unoccupied portion or "end volume" of the bore VB2 is less than VC.

The bulb has a total volume VB1. The bulb produces less than a unit volume of displacement in the cryostraw when the bulb is squeezed and VB1 is reduced by a unit volume. Because the walls of the bulb are compressible, VB1 can be initially reduced without reducing VB2.

In a preferred embodiment, the ratio of VB1 to VB2 is very large to maximize the "feel" of the bulb while minimizing volume displacement in the cryostraw. The total volume displacement produced by squeezing the bulb to its maximum compression is less than VC so that the cryostraw can not be over admitted. The apparatus is also constructed to emit the entire volume of material contained in the cryostraw by manually squeezing the bulb once.

A sheath surrounds at least the base portion of the cryostraw. The sheath prevents the cryostraw from deforming when the bulb is squeezed. A support ring abuts the second end of the bulb and prevents distortion of the cross-sectional shape of the flat second end when the bulb is compressed.

A flexible, outer casing surrounds the bulb. The casing preferably encapsulates the bulb and the outer connection intersect between the bulb and the cryostraw. The outer casing provides a complete secondary seal on the first end of the cryostraw. The casing can be initially compressed without causing any volume displacement in the cryostraw.

The tip of the cryostraw can be heat sealed to completely encapsulate the material in the cryostraw. The integrity of the heat seal can be immediately tested by squeezing the bulb and observing the column of fluid in the cryostraw. If the column does not move, the seal is intact. If fluid is expelled, the seal is breached and must be repaired or replaced. The process of sealing the tip and checking the seal is performed using a single hand.

BRIEF DESCRIPTION OF THE DRAWINGS

FIG. 1 is top plan of an apparatus in accordance with an embodiment of the invention;

FIG. 2 is a side elevation of the apparatus shown in FIG. 1;

FIG. 3 is an exploded top plan of the apparatus shown in FIG. 1;

FIG. 7 is graph showing the relationship between volumetric compression of the bulb portion of the apparatus, represented by "Squeeze" on the X axis, versus volumetric displacement in the cryostraw, represented by "Column Height" on the Y axis;

FIG. 11 is a cross section of an apparatus in accordance with an additional embodiment of the invention;

FIG. 12 is a cross-section of the collapsible plug of the apparatus of FIG. 11;

FIGS. 13a and 14a are side elevations of alternative plugs for use in the apparatus of FIG. 11;

FIGS. 13b and 14b are front elevations of the plugs of FIGS. 13a and 14a, respectively;

FIG. 15 is a top plan of an apparatus in accordance with an additional embodiment of the invention;

FIG. 16 is an is an exploded top plan of the apparatus shown in FIG. 15;

FIG. 17 is an enlarged, fragmentary, cross-section of the apparatus shown in FIG. 15 showing the swage on the end of the cryostraw; and FIG. 18 is an end view of the cryostraw and swage of FIG. 17.

DETAILED DESCRIPTION OF PREFERRED EMBODIMENTS

Figure 4:
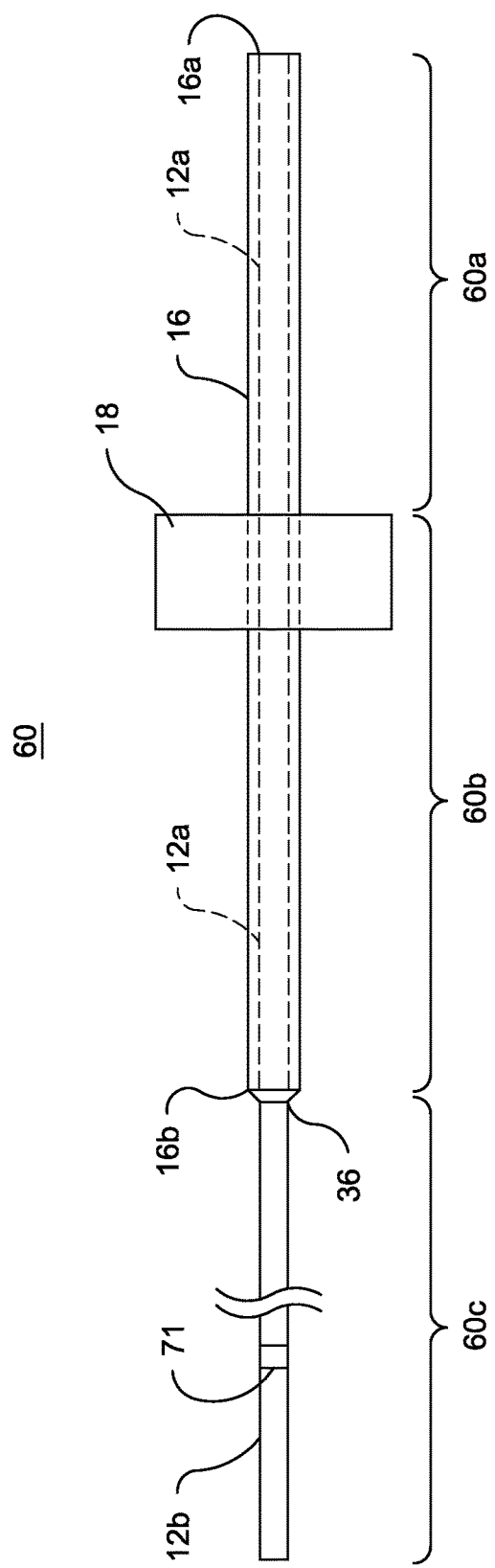
FIG. 4 is an enlarged, fragmentary side elevation of the straw assembly of the apparatus shown in FIG. 1.

For the purpose of illustrating the invention, several embodiments of the invention are shown in the accompanying drawings. However, it should be understood by those of ordinary skill in the art that the invention is not limited to the precise arrangements and instrumentalities shown therein and described below. Throughout the specification, like reference numerals are used to designate like elements.

The apparatus in accordance with a first embodiment of the invention is illustrated in FIGS. 1-8. Referring to FIG. 1, the apparatus, designated generally by reference numeral 10, has a bulb portion 10a and a cryostraw portion 10b. In this embodiment, the apparatus 10 includes an elongate cryostraw 12 connected in fluid communication with a metering bulb 14. A sheath 16 surrounds and supports one end portion of the cryostraw 12. A ring 18 surrounds the sheath 16, and abuts and supports the front end 14b of the bulb 14. An outer casing 20 forms a secondary seal around the entire bulb, the bulb/straw outer intersect and the sheath/straw outer intersect. The bulb portion 10a can be held between the thumb and forefinger and squeezed to admit and/or expel material through the tip 25 of the cryostraw 12.

The cryostraw 12 preferably comprises precision plastic tubing having open ends. The cryostraw material should preferably be flexible and capable of being formed or manufactured to very small constant diameters, and very close dimensional tolerances.

The cryostraw material should be heat sealable and also remain durable at very low temperatures and, in particular, durable when immersed in liquid nitrogen and then thawed. For example, the cryostraw 12 may be made from polycarbonate.

The diameter and wall thickness of the cryostraw 12 should be minimized to reduce thermal mass and to maximize the rate at which the reproductive material contained within the cryostraw 12 is cooled. However, the inner diameter but must be large enough to admit human reproductive material immersed in a fertilization solution. In the embodiment shown in FIG. 1, the cryostraw 12 has an inner diameter of about 0.010 in. and an outer diameter of about 0.015 in.

The overall length of the cryostraw 12 may vary but should be long enough so that a technician can easily grasp the bulb portion 10a and maneuver the tip 25 proximate the reproductive material contained in a fertilization dish while viewing the material under a microscope. The cryostraw 12 should preferably be short enough so that the apparatus fits within a standard cryovial, which is typically about ½ in. in diameter and about 3 in. long. In a preferred embodiment, the overall length of the cryostraw 12 is about 2-½ in.

Figure 6:
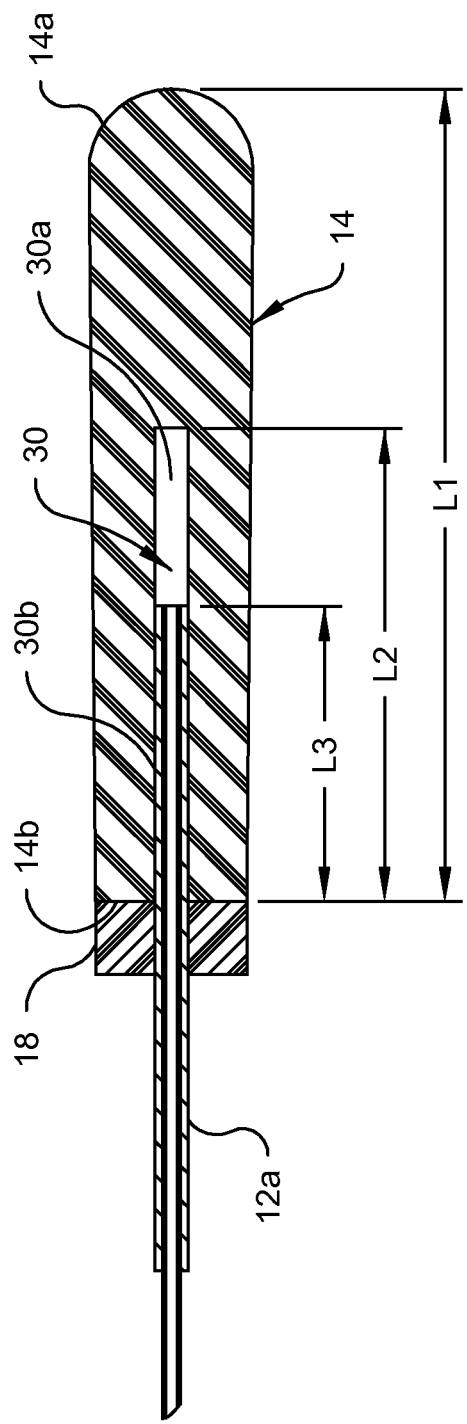
FIG. 6 is an enlarged, fragmentary, cross section view of the apparatus shown in FIG. 1 showing the bulb and the connection interface with the straw assembly.

Referring to FIGS. 3 and 4, the cryostraw 12 is generally divided into a base portion 12a at one end and a tip portion 12b at the other end. As best seen in FIGS. 4 and 6 and described below, the base portion 12a is surrounded by the sheath 16, which supports the cryostraw 12 and prevents it from collapsing when the bulb 14 is squeezed.

Figure 5:
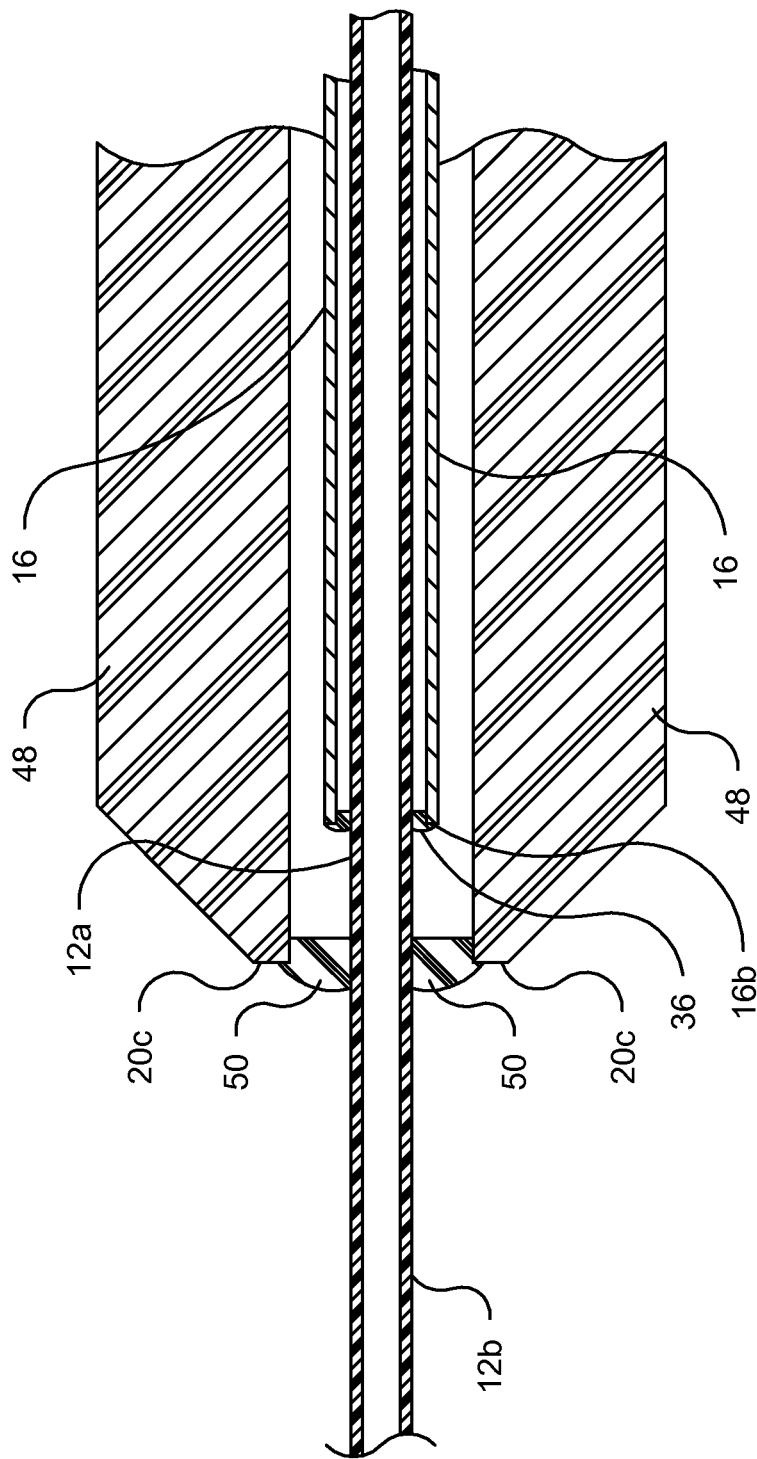
FIG. 5 is an enlarged, fragmentary cross-section of the apparatus shown in FIG. 1 showing the sealed interface between the cryostraw and the sheath, and the sealed interface between the cryostraw and the outer casing.

Referring to FIG. 5, the inner diameter of the sheath 16 is slightly larger than the outer diameter of the cryostraw 12. In the embodiment illustrated in FIGS. 1-8, the clearance is approximately 0.005 in., which enables the cryostraw 12 to be threaded through the sheath 16 during assembly without damaging the cryostraw 12. Referring to FIGS. 4 and 5, the sheath 16 is secured to the cryostraw 12 at the outer intersect by adhering the front end 16b of the sheath 16 to the outer surface of the cryostraw 12. As best seen in FIG. 5, the adhesive 36 contacts both the axial end surface and a portion of the radial interior end surface of the sheath 16. For additional security, the sheath 16 may also be crimped to the cryostraw to provide an additional mechanical connection.

The sheath 16 is preferably made of a material having sufficient rigidity to prevent distortion of the cryostraw 12 when the bulb 14 is squeezed to its maximum compression. In a preferred embodiment, the sheath 16 comprises type 304 stainless hypodermic tubing having an outer diameter of about 0.032 in. and an inner diameter of about 0.020 in. Other rigid metal or plastic materials may be used so long as the material remains durable at very low temperatures and, in particular, durable when immersed in liquid nitrogen and then thawed.

Referring to FIG. 4, the support ring 18 is fixed medially to the outer surface of the sheath 16. In a preferred embodiment, the support ring 18 has an outer diameter approximately equal to the outer diameter of the bulb 14. The support ring 18 also preferably has an inner diameter slightly smaller than the outer diameter of the sheath 16, which creates an interference fit for the support ring 18.

The support ring 18 may be made of any rigid material that remains durable at extremely low temperatures. For example, the support ring 18 may be made from any type of homopolymer or copolymer plastic such as ABS plastic or Delrin.

Together, the cryostraw 12, support ring 18 and sheath 16 form the straw assembly 60 as shown in FIG. 4. The rear section 60a is inserted into and connected in fluid communication with the metering bulb 14. The middle section 60b extends from the front end 26 of the bulb 14 and terminates at the front end 16b of the sheath 16. The front section 60c extends from the front end 16b of the sheath 16 to the tip 25 of the cryostraw 12.

The support ring 18 abuts the front face 14b of the bulb 14. During assembly, the support ring 18 limits the distance the rear section 12a of the cryostraw 12 is inserted into the bulb 14, thereby acting as a stop.

The support ring 18 also prevents the front end 14b of the bulb 14 from distorting when the bulb 14 is compressed. During compression, the support ring 18 maintains a circular cross section proximate the front face 14b of the bulb 14, which maintains a good seal between the bulb 14 and the sheath 16.

The displacement bulb 14 is connected to the rear section 60a of the straw assembly 60. Referring to FIG. 6, in a preferred embodiment, the bulb 14 comprises a solid mass of compressible material having a generally-cylindrical shape with an outer radius R1, an overall length L1, a flat front end 14b, and a semi-hemispherical, rear end 14a. An axial bore 30 having a radius R2 extends from the front end 14b a distance L2, which is less than L1. The radius of the bore R2 is less than R1. The dimensions of the bulb 14 are selected so that it can be grasped easily between the thumb and fore finger and squeezed easily to admit and dispense material from the cryostraw 12.

The bulb 14 is preferably made from any material having good compressibility and being durable at very low temperatures and, in particular, durable when immersed in liquid nitrogen and then thawed. In a preferred embodiment, the bulb material comprises 20 durometer silicone.

Referring to FIG. 6, the front portion 30b of the axial bore 30 is occupied by the rear section 60a of the straw assembly 60, which extends a distance L3 therein. The rear end portion 30a of the bore 30 is unoccupied and can be compressed when the bulb 14 is squeezed. The volume of the rear end portion 30a or "end volume" can be very precisely controlled by selecting the inner radius R2 of the bore 30 and controlling the distance L3 the straw assembly 60 is inserted into the bore 30. The end volume VB2 is equal to $\Pi(R2)^2(L2-L3)$. For example, in the embodiment disclosed in FIGS. 1-8, the end volume can be controlled to a tolerance of about ¼ microliter. The apparatus is preferably designed so that the end volume is less than the volume of the cryostraw 12. As a result, the cryostraw 12 can not be over admitted. In a preferred embodiment, the end volume is about half the volume of the cryostraw 12.

The outer casing 20 surrounds the entire bulb 14 (including the entire rear section 60a of the straw assembly), the entire middle section 60b of the straw assembly 60, and a short length of the front section 60c. As best seen in FIG. 3, the outer casing 20 comprises a length of flexible tubing having a reduced-diameter front end 20c and sealed rear end 20a. The middle section 20b of the casing 20 has an inner diameter that is slightly larger than the outer diameter of the bulb 14. Preferably, the diameter of the outer casing 20 is at least about 0.014 in. larger than the diameter of the bulb 14, which is the preferred minimum clearance needed to give the technician a good feel for compressing the casing 20. The front end 20c has an inner diameter slightly larger than the outer diameter of the sheath 16. The reduced-diameter front end 20c is formed by crimping the tubing with opposed dies, which form opposed fins 48. The sealed rear end 20c is preferably heat sealed. A best seen in FIG. 5, the front end 20c of the outer casing 20 is sealed to the outer surface of the cryostraw 12 at the outer intersect. The seal is formed using UV curable adhesive 50, such as flexible ultra violet acryate, that adheres to both the axial end surface and a portion of the inner radial surface of the casing 20.

The casing 20 should be made from a material that is flexible and remains durable at very low temperatures and, in particular, durable when immersed in liquid nitrogen and then thawed. For example, the casing 20 may be made from any thermoplastic elastomer. The casing wall should be thick enough so that the casing 20 retains its shape after squeezing, freezing and thawing. Preferably, the casing wall should also be thick enough so that it provides a manually-detectable resistance to squeezing. In other words, the casing 20 should have sufficient rigidity so that the user feels deflection of the casing 20 before the bulb 14 begins to deflect. In the embodiment shown in FIGS. 1-8, the casing 20 has a wall thickness of about 0.006 in.

In a preferred embodiment, the apparatus 10 is used for separating and storing human reproductive material. In this embodiment, the volume of the cryostraw 12 is very small, for example, 0.9 to 1.1 microliters. Even though the bulb 14 has a very large overall volume VB1 compared to the cryostraw 12, the intake volume displacement produced by the bulb 14 in the cryostraw 12 is limited so that the cryostraw 12 can not be over admitted. Intake volume displacement in the cryostraw 12 is limited in this embodiment by controlling the end volume VB2 to a volume less than the internal volume VC of the cryostraw 12. In the embodiment shown in FIGS. 1-8, VB2 is about ½VC. Therefore, no matter how hard or far the technician squeezes the bulb 14 of the apparatus 10, the cryostraw 12 will not be over admitted and the material will not be admitted into the bulb 14.

The apparatus also transforms and reduces the volume displacement produced in the cryostraw 12 per unit of volume displacement of the overall volume VB1 of the bulb 14. When the bulb 14 is squeezed and reduced overall by a unit volume, the displacement produced in the cryostraw 12 is substantially less than a unit volume.

The graph of FIG. 7 shows the correlation, i.e., reduction ratio, between displacement in the cryostraw ΔVC, represented on the Y axis as a function of column height in the cryostraw, versus the displacement of the overall volume of the bulb ΔVB1, represented on the X axis as a function of the distance the bulb 14 is compressed from its relaxed condition. The data was generated by compressing the bulb using a pair of calipers until the end volume was completely collapsed. The calipers were axially located above the end volume. The cryostraw tip was placed in a beaker of water and the calipers were incrementally released. The height of the water drawn into the cryostraw was measured for each incremental release of the calipers.

Referring to the graph of FIG. 7 and the illustrations of FIGS. 8a-e, the reduction ratio, represented by the slope of the curve at various points, varies as the bulb 14 is compressed from its relaxed state to its maximum compression state. FIGS. 8a-e show the bulb portion 10a in five progressively compressed conditions.

Figure 8A:
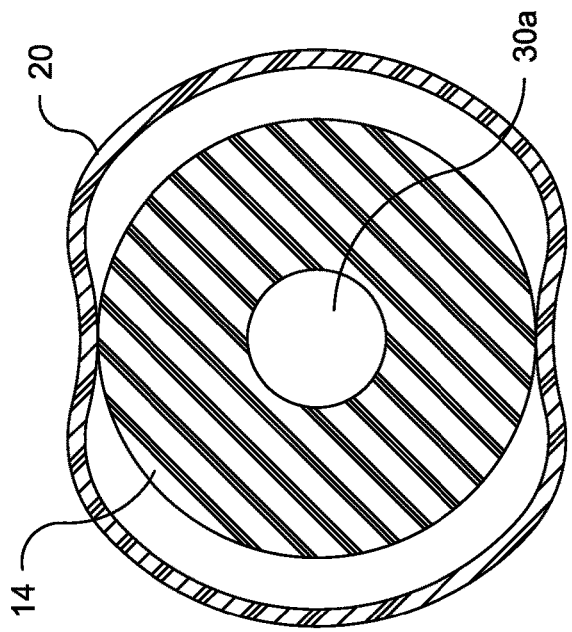
FIGS. 8a-e are cross-sections taken along lines 8-8 of FIG. 1 at progressive conditions of compression of the bulb portion that correspond with the graph of FIG. 7.
Figure 8B:
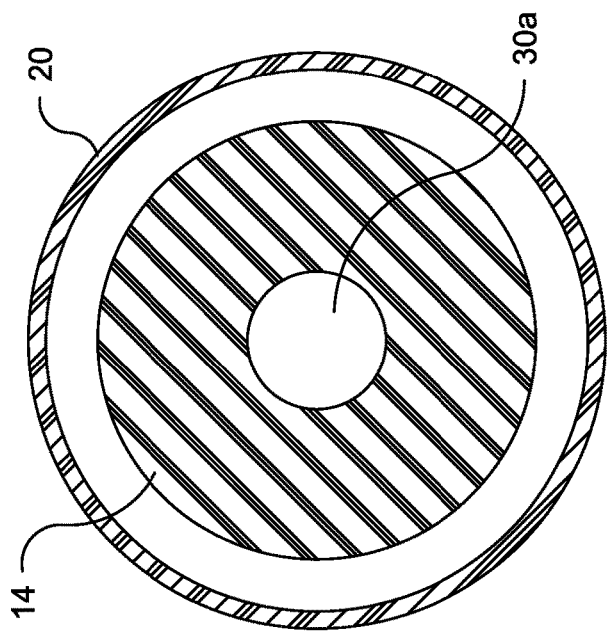

In condition 1, FIG. 8a, the bulb portion 10a of the apparatus 10 is completely relaxed and subject to no compressive load. In condition 2, FIG. 8b, only the outer casing 20 is deflected after an initial compressive load is applied. No displacement in the cryostraw 12 occurs in the first compressive phase from condition 1 to condition 2 since the bulb 14, and in particular the end volume 30a, is not compressed. In the first compressive phase, the casing 20 desensitizes the apparatus by preventing any volumetric displacement in the cryostraw 12.

Figure 8C:
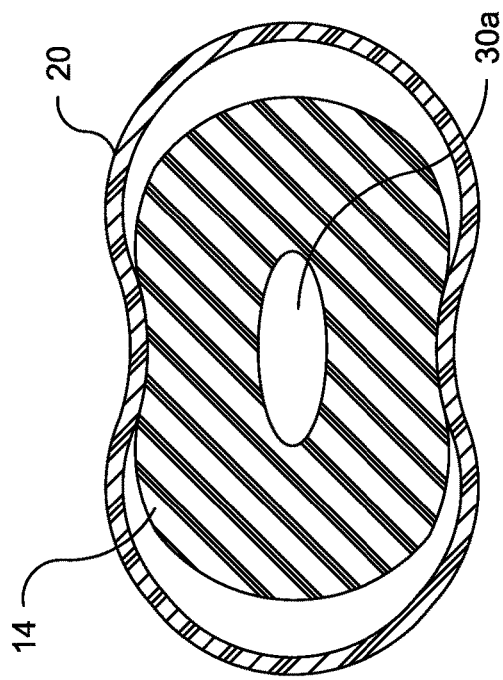

After the compressive load increases in condition 3, FIG. 8c, the bulb wall is substantially compressed while the end volume is only slightly compressed and slightly elongated because the bulb material is very soft and compressible. In the second compressive phase from condition 2 to condition 3, a small volumetric displacement occurs in the cryostraw 12 due to initial compression of the end volume. In the second compressive phase, the bulb wall's compressibility desensitizes the apparatus by transforming the volumetric displacement in the cryostraw 12 by a first reduction ratio. In the example shown in FIG. 7, the ratio of cryostraw displacement to bulb compression is approximately 10:1.

Figure 8D:
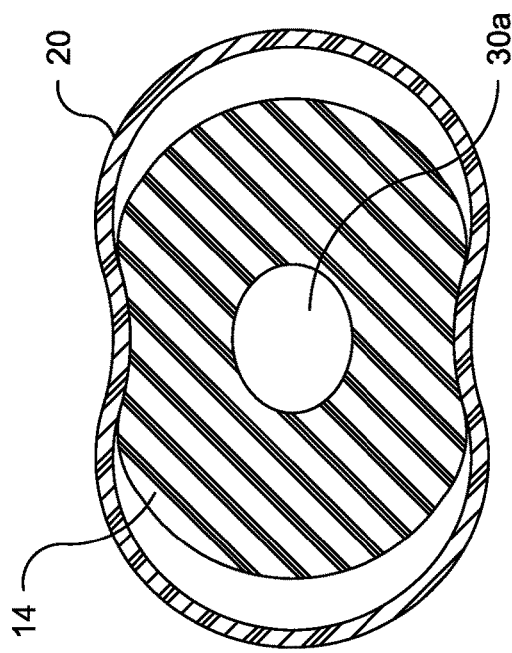

After the compressive load further increases in condition 4, FIG. 8d, the bulb wall is substantially compressed while the end volume becomes substantially compressed and substantially elongated. In the third compressive phase from condition 3 to condition 4, the bulb wall's compressibility, and the changing geometric cross section of the cavity from circular to ovular, desensitizes the apparatus by transforming the volumetric displacement in the cryostraw 12 by a second reduction ratio. In the example shown in FIG. 7, the ratio of cryostraw displacement to bulb compression is approximately 28:1.

Figure 8E:
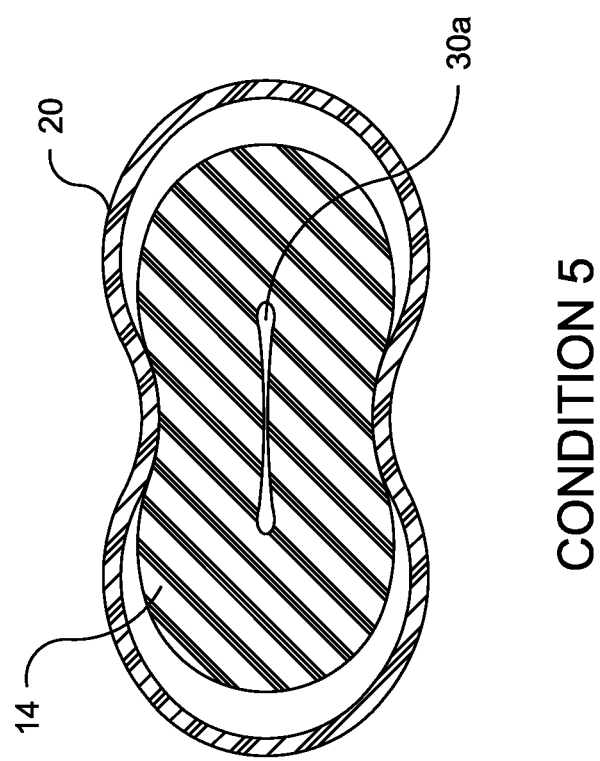

After a maximum compressive load in condition 5, FIG. 8e, the bulb wall is substantially compressed while the end volume is completely compressed. In the fourth compressive phase from condition 4 to condition 5, the rapidly changing geometric cross section of the end volume from ovular to linear, desensitizes the apparatus by transforming the volumetric displacement in the cryostraw 12 by a third reduction ratio. In the example shown in FIG. 8, the ratio of cryostraw displacement to bulb compression is approximately 7:1.

The graph shows that the average ratio of cryostraw displacement to bulb compression is about 15:1. The graph also shows that the smallest volumetric reduction ratio occurs in compressive phase 3 between conditions 3 and 4 when the technician has the greatest "feel" for the apparatus while much larger volume reduction ratios occur in compressive phases 2 and 4. As a result, pipetting error is reduced in the initial compressive phase when the technician is first developing a feel for the apparatus. Similarly, pipetting error is minimized in the final compressive phase when the technician may over-squeeze the apparatus. In fact, as described above, the apparatus is designed so that the reproductive material will not be over admitted through the cryostraw and into the bulb 14.

The apparatus is designed to dispense the entire contents of the cryostraw 12 by squeezing the bulb 14 only once because air does not leak from the bulb 14 to the atmosphere. As described above, the support ring 18 prevents the front end of the bulb 14 from distorting when the bulb 14 is compressed, thereby maintaining a good seal between the bulb 14 and the base portion 12a of the cryostraw 12. Further, the casing 20 provides a secondary seal between the bulb 14 and the cryostraw 12. The secondary seal prevents air from leaking out of the cryostraw 12 while compressing the bulb 14, and prevents liquid nitrogen from leaking into the cryostraw 12 during storage.

In contrast with prior art methods, a technician can use the apparatus using a single hand. In a preferred embodiment, the apparatus is used according to the following steps: (1) holding the bulb portion of the apparatus between the thumb and forefinger; (2) admitting a small amount of fertilization fluid into the cryostraw by squeezing the bulb portion, immersing the tip into the fertilization fluid, and then releasing the bulb; (3) expelling a portion of the fluid from the cryostraw by squeezing the bulb portion once again; (4) admitting the human reproductive material by locating the tip proximate the material and then releasing the bulb so that the material is admitted into the cryostraw with a column of fertilization fluid surrounding the material on both sides. The aforementioned procedure can be done very easily and precisely with one hand since the bulb portion and cryostraw are integrally formed.

Once the human reproductive material is successfully admitted into the cryostraw, the tip is sealed simply by contacting the tip to a heat source and fusing it closed. Instantly thereafter, the technician can check the integrity of the seal by squeezing the bulb once again and observing the column of fluid within the cryostraw. If the column does not move, the seal is intact. If fluid is expelled, the seal is breached and must be repaired or replaced. The process of sealing the tip and checking the seal can also be performed using a single hand.

Figure 9:
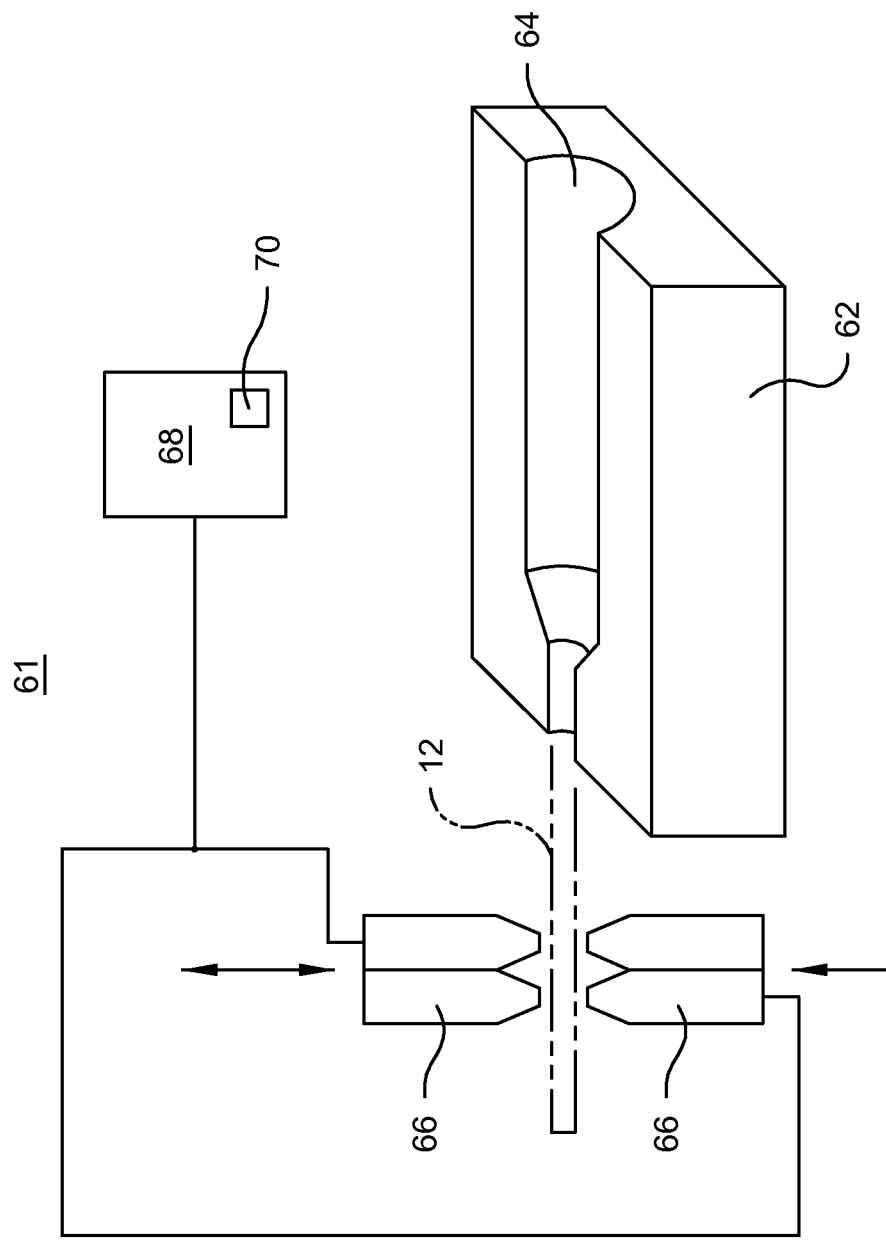
FIG. 9 is a schematic view of a device for automated sealing of the tip of the apparatus show in FIG. 1.

To ensure the integrity of the tip seal, an automated sealing device may be provided, which greatly reduces sealing error and provides a more consistent seal. Referring to FIG. 9, the tip sealing device 61 may comprise, for example, a base 62 having a recess 64 molded to the shape of the bulb portion 10a of the apparatus 10. One or more pairs of heated, crimping heads 66 are disposed adjacent the base 62. The heads 66 extend and retract relative to one another and the cryostraw portion 10b (shown in phantom) of the apparatus 10 extending from the base 62. Cyclic movement of the heads is controlled by a programmable controller 68, which controls variables such as contact time, head surface temperature, and cycle time. The sealing cycle is initiated by depressing a button 70 on the controller after the apparatus 10 is loaded in the base 62.

In a preferred embodiment, the cryostraw 12 may be provided with a pair of transversely-oriented lines 71 located generally medially along the length of the cryostraw 12 as seen in FIG. 4. The lines 71 define a target area at which the human reproductive material is preferably located so that an adequate amount of media is located on opposed sides of the material. Because the apparatus 10 provides very precise metering, a technician can easily land the material within the target area.

Once the apparatus is sealed, it is inserted in a liquid nitrogen (LN) filled cryovial, which is then deposited into a cryotank filled with LN for rapid freezing. As described above, the apparatus is made from materials that remain durable at extremely low temperatures to insure the material is protected from damage or contamination. At a future date, the material may be retrieved by removing the apparatus from the cryotank, thawing the apparatus and its contents, severing the sealed tip, and expelling the reproductive material from the apparatus by simply squeezing the bulb 14. Each of these functions can be performed using a single hand.

In a preferred embodiment, the components of the apparatus are assembled in the following order. Initially, the support ring 18 is pressed onto the midpoint of the sheath 16. The bulb 14 is pushed onto the rear section of the sheath 16 until the bulb 14 contacts the support ring 18. The cryostraw 12 is then threaded through the metering sheath 16 until it is coterminous with or extends slightly past the rear end 16a of the metering sheath 16. Ultra violet (UV) curable adhesive is applied to the cryostraw/sheath outer intersect, i.e. the joint between the front end 16b of the sheath and the outer surface of the cryostraw 12, thereby forming the straw assembly 60. The straw assembly is inserted through the open back end of the casing 20 in the form shown in FIG. 2 until the support ring 18 contacts the internal taper formed in the front of the casing 20. UV curable adhesive is applied to the cryostraw/casing outer intersect, i.e., the joint between the front end 20b of the casing 20 and the outer surface of the cryostraw 12. Finally, the rear end 20a of the outer casing 20 is heat sealed to form an airtight casing surrounding the bulb 14.

The outer casing 20 shown in FIG. 2 is formed by reducing the diameter of one end of a preselected length of tubing using a pair of heated crimping dies. Before the crimping dies contact and squeeze the tube, a cylindrical rod is inserted into one end of the tube. The rod prevents the tube from collapsing and occluding the central bore of the tube. As the dies press and reshape the tube, excess tube material is squeezed radially outwardly from the die and form fins 48. The fins 48 are then longitudinally sheared or cut in the form shown in FIG. 2. This method is described in greater detail in U.S. Pat. No. 6,531,098, which is incorporated herein by reference. The fins 48 provide reinforcement at the point of highest stress on the casing 20, thereby acting as a strain relief.

Figure 10:
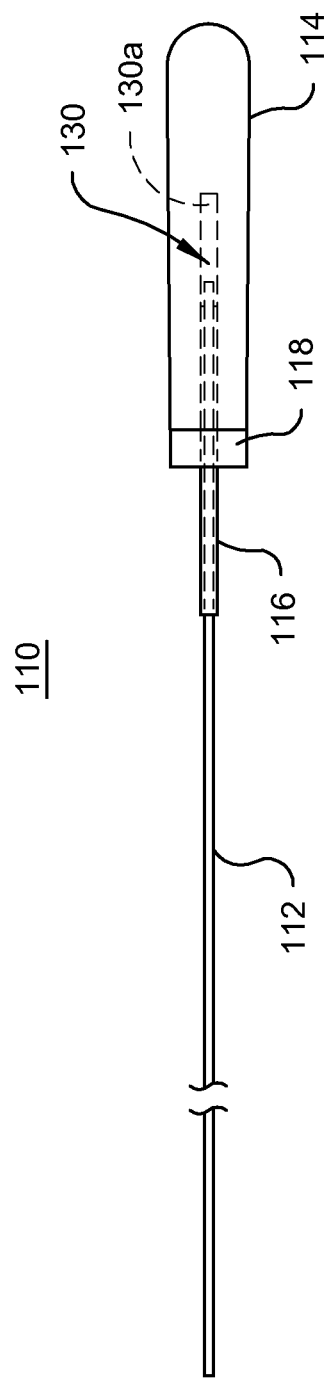
FIG. 10 is a side elevation of an apparatus in accordance with a further embodiment of the invention.

The apparatus in accordance with another embodiment of the invention is shown in FIG. 10. The apparatus 110 is similar in construction to the apparatus 10 described and illustrated above. However, in this embodiment, the apparatus does not include the outer casing 20. In this embodiment, intake volume displacement in the cryostraw 112 is limited by limiting the "end volume" VB2 of the rear end portion 130a of the bulb bore 130 to a volume less than the internal volume VC of the cryostraw 112. Therefore, no matter how hard or far the technician squeezes the bulb portion of the apparatus 110, the cryostraw 112 will not be over admitted and the human reproductive material will be located within the cryostraw 112.

The apparatus 110 also transforms and reduces the volume displacement produced in the cryostraw per unit of displacement of the overall volume VB1 of the bulb 114. Since the apparatus 110 has no outer casing, displacement in the cryostraw 112 occurs after initial compression; however, the bulb wall's compressibility and the changing geometric cross section of the end volume, desensitizes the apparatus by reducing the volumetric displacement in the cryostraw 112 in the same manner as described above with respect to the apparatus 10 shown in FIGS. 1-8.

An apparatus in accordance with an additional embodiment of the invention is shown in FIGS. 11 and 12. The apparatus 210 is similar in construction to the apparatus 10 described and illustrated above. However, in this embodiment, the apparatus 210 does not include silicon bulb 14 but includes a plug 270 inserted into the casing 220. The plug 270 may be rigid or compressible. In this embodiment, positive and negative pressure is created in the cryostraw 212 by compressing and releasing the outer casing 220. The plug 270 limits the distance the casing 220 can be compressed, thereby limiting the volumetric displacement generated by the casing 220. If the plug 270 is compressible, the plug 270 also desensitizes the apparatus by transforming/reducing the volumetric displacement in the cryostraw 212.

The shape and size of the plug 270 may vary. FIGS. 12a-13b illustrate two additional examples of plugs 370, 470, respectively. If the plug is asymmetrical and can only be compressed along one axis, such as shown in FIGS. 14a and 14b, the plug 470 should be oriented in such a way that the fins 248 are co-planar with the preferred, opposed depression points on the casing. This construction urges the technician to relocate her fingers to the preferred depression points if she feels the sharp edge of the fins impinging on her fingers.

An apparatus in accordance with yet a further embodiment of the invention is shown in FIGS. 15-18. The apparatus 310 is similar in construction to the apparatus 10 described and illustrated above. However, in this embodiment, the apparatus 310 does not include a support sheath 16. Instead, the cryostraw 312 is inserted into and directly contacts the bulb 314.

In this embodiment, the cryostraw 312 includes a swage 381 on its outer surface proximate the end of the base portion 312a. The swage 381 may have the barbed shape best seen in FIG. 17 or other more rounded shapes so long as the outer diameter of the swage 381 is larger than the outer diameter of the cryostraw 312. The swage 381 secures the cryostraw 381 in the bulb 314 and helps prevent the end of the base portion 312a of the cryostraw 312 from collapsing when the bulb 320 is squeezed.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. Apparatus for separating individual human reproductive material from a fertilization dish and storing the material in a cryotank for future fertilization and implantation, comprising:
   a) an elongate cryostraw having first and second open ends, a channel extending between said ends, and an internal, calibrated volume VC;
   b) a displacement bulb connected to the first end of said cryostraw for admitting and emitting the material into said cryostraw, said bulb having an overall volume VB1 and an internal cavity with a compressible end volume VB2; and, c) an outer casing surrounding said bulb which defines a substantially empty space between the casing and the bulb such that when squeezed the casing can deflect before the bulb deflects preventing any volumetric displacement in the cryostraw, wherein said bulb produces less than a unit volume of displacement in said cavity when the bulb is squeezed and its volume VB1 is reduced by said unit volume.

2. The apparatus recited in claim 1, wherein the volume of displacement produced in the cryostraw by squeezing said bulb from its relaxed condition to its maximum compression is less than VC.

3. The apparatus recited in claim 1, wherein said bulb comprises a solid mass of compressible material having an internal bore of constant diameter with a rear portion defining the cavity.

4. The apparatus recited in claim 3, wherein a portion of said cryostraw is inserted into and occupies a front portion of said bore and does not occupy a rear portion of said bore.

5. The apparatus recited in claim 4, wherein the volume of the unoccupied rear portion of said bore is less than the volume of said cryostraw.

6. The apparatus recited in claim 4, including a sheath surrounding at least the portion of said cryostraw that is inserted into said bulb, said sheath preventing said cryostraw portion from deforming when said bulb is squeezed.

7. The apparatus recited in claim 3, wherein said bulb is cylindrical and has a semi-hemispherical first end and a flat second end, and said bore is cylindrical and extends inwardly and co-axially from said second end.

8. The apparatus recited in claim 7, including a support ring abutting the second end of said bulb and preventing distortion of the cross-sectional shape of said flat second end when said bulb is compressed.

9. The apparatus recited in claim 1, wherein said outer casing forms a complete, secondary seal on the first end of said cryostraw.

10. The apparatus recited in claim 1, wherein the casing can be compressed without causing any volume displacement in said cryostraw.

11. The apparatus recited in claim 1, wherein the average ratio of cryostraw displacement to bulb compression is at least about 15:1.

12. The apparatus recited in claim 1, wherein said bulb is constructed and arranged to emit the entire volume of material contained in said cryostraw by manually squeezing said bulb once.

13. The apparatus recited in claim 1, wherein VB1 can be reduced without reducing VB2.

14. Apparatus for separating individual human reproductive material from a fertilization dish and storing the material in a cryotank for future fertilization and implantation, comprising:

a) an elongate cryostraw having a first open end and second heat-sealable open end, a channel extending between said ends, and an internal, calibrated volume VC;

b) a displacement bulb connected to said first end of said cryostraw at a connection interface for admitting and emitting the material into said cryostraw, said bulb having:

a) a total volume VB1;

b) an internal cavity with a compressible end volume VB2;

c) a first seal with the first end of said cryostraw; and, d) means for limiting the intake volume displacement produced in said cryostraw to an amount less than VC no matter how far the bulb is squeezed from its relaxed condition; and e) an outer casing surrounding said bulb which defines a substantially empty space between the casing and the bulb such that when squeezed the casing can deflect before the bulb deflects.

15. The apparatus recited in claim 14, including a second seal on the first end of said cryostraw.

16. The apparatus recited in claim 15, wherein said second seal comprises a casing surrounding the bulb and the connection interface between the bulb and the cryostraw.

17. The apparatus recited in claim 14, including integrated means for testing the integrity of a heat seal applied to said second open end.

18. Apparatus for separating individual human reproductive material from a fertilization dish and storing the material in a cryotank for future fertilization and implantation, comprising:

a) an elongate cryostraw having first and second open ends, a channel extending between said ends, and an internal, calibrated volume VC;

b) a displacement bulb connected to the first end of said cryostraw at a connection interface for admitting and emitting the material into said cryostraw, having:
  i) a solid body made of compressible material and having a total volume VB1, and;
  ii) an internal cavity having a compressible end volume less than VC, c) a flexible outer casing encapsulating said bulb and the connection interface between said bulb and said cryostraw, said casing defining a sealed substantially empty space between the casing and the bulb such that when squeezed the casing can deflect before the bulb begins to deflect.

19. The apparatus recited in claim 18, wherein said bulb comprises:

a) a cylindrical, solid mass having first and second axial ends, an outer radius R1 and a length L1; and, b) an axially-extending bore in the first end having a length L2 that is less than L1 and a radius R2 that is less than R1.

20. The apparatus recited in claim 19, wherein said cryostraw has a base portion that is inserted a predetermined distance L3 into said bore so that the end volume of the bore $\Pi(R2)^2(L2-L3)$ is less than VC.

21. The apparatus recited in claim 20, wherein the radial surface of at least the base portion of said cryostraw is enveloped in a sheath.

22. The apparatus recited in claim 21, wherein said sheath prevents the base portion from collapsing when the bulb is compressed by squeezing.

23. The apparatus recited in claim 22, including an annular support ring on the first end of said bulb that prevents annular distortion of the first end of the bulb when the bulb is compressed by squeezing.

24. The apparatus recited in claim 18, wherein the bulb can be initially compressed without causing any volume displacement in the cryostraw.

* * * * *